US006279792B1

United States Patent
Neal

(10) Patent No.: US 6,279,792 B1
(45) Date of Patent: Aug. 28, 2001

(54) APPARATUS FACILITATING THE REMOVAL OF A LATEX GLOVE FROM THE HAND OF A WEARER

(76) Inventor: Thomas G. Neal, 4061 Hatcher Hollow Rd., Walland, TN (US) 37886

( * ) Notice: Subject to any disclaimer, the term of this patent is extended or adjusted under 35 U.S.C. 154(b) by 0 days.

(21) Appl. No.: 09/641,659

(22) Filed: Aug. 18, 2000

(51) Int. Cl.⁷ .................................................. A47G 25/80
(52) U.S. Cl. ................................................................ 223/111
(58) Field of Search ..................... 223/111, 112, 223/120, 1

(56) References Cited

U.S. PATENT DOCUMENTS

| | | | | |
|---|---|---|---|---|
| D. 259,299 | * | 5/1981 | Vreeken | D2/378 |
| D. 275,239 | * | 8/1984 | Raso | D2/378.2 |
| 2,741,410 | * | 4/1956 | La Violette | 223/111 |
| 4,228,935 | * | 10/1980 | Madray | 223/111 |
| 4,898,309 | * | 2/1990 | Fisher | 223/111 |
| 5,050,784 | * | 9/1991 | Turner | 223/114 |
| 5,082,154 | * | 1/1992 | French | 223/112 |
| 5,152,439 | * | 10/1992 | Simons | 223/114 |

* cited by examiner

Primary Examiner—Bibhu Mohanty
(74) Attorney, Agent, or Firm—Michael E. McKee

(57) ABSTRACT

An apparatus facilitating the removal of a pair of latex gloves from the hands of a wearer as the forearms of the wearer are slid therealong utilizes a support base and a pair of blade-like members which are secured to the base in a stationary relationship therewith and in a side-by-side relationship. Each blade-like member includes an arcuate edge which extends forwardly of the base so that as a wearer of a pair of rubber gloves slides the inside surfaces of his forearms in a rearward direction along the surfaces of the blade-like members, the cuff portions of the glove accept and become hooked upon the arcuate edges of the blade-like members so that continued movement of the forearms rearwardly along the blade-like members backs the hands out of the gloves.

7 Claims, 4 Drawing Sheets

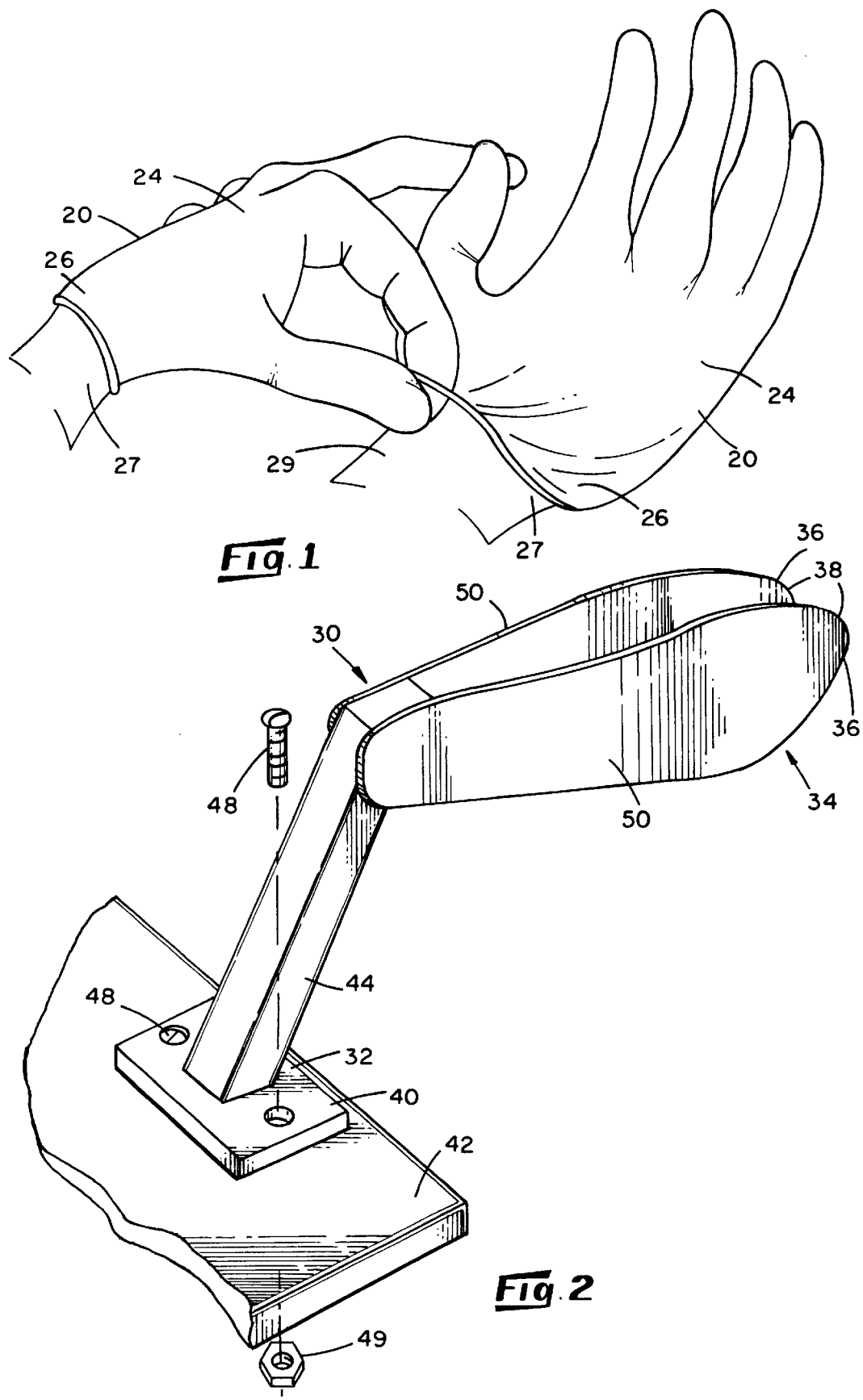

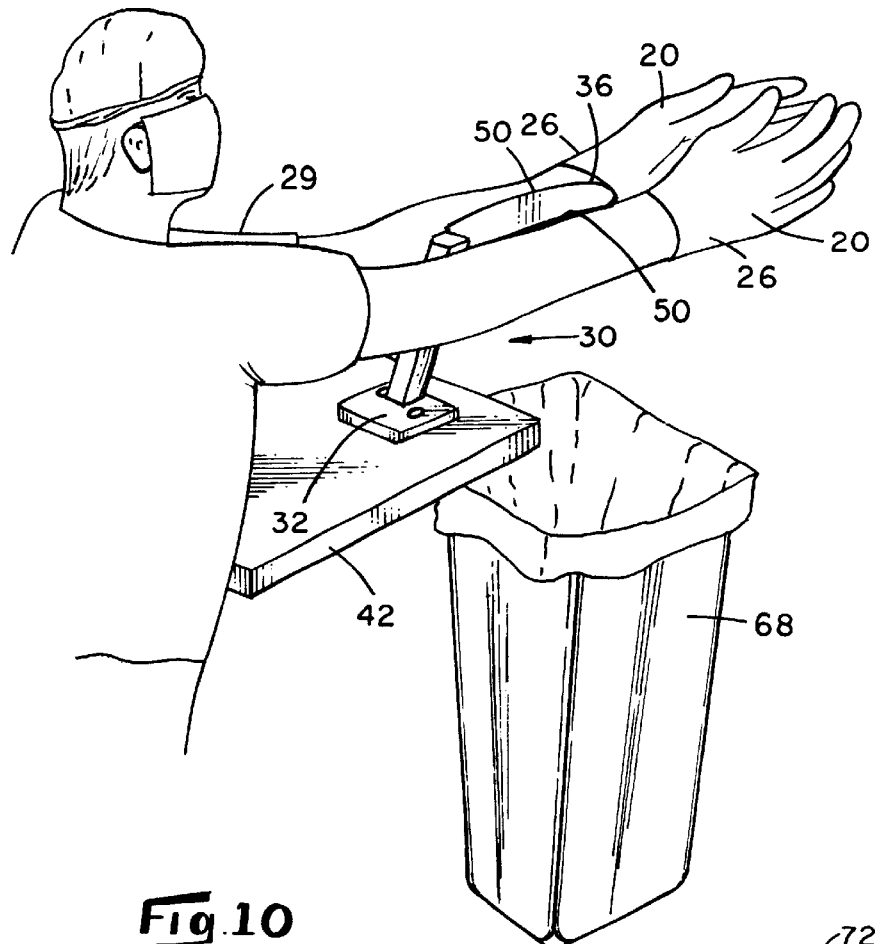
_Fig.10_
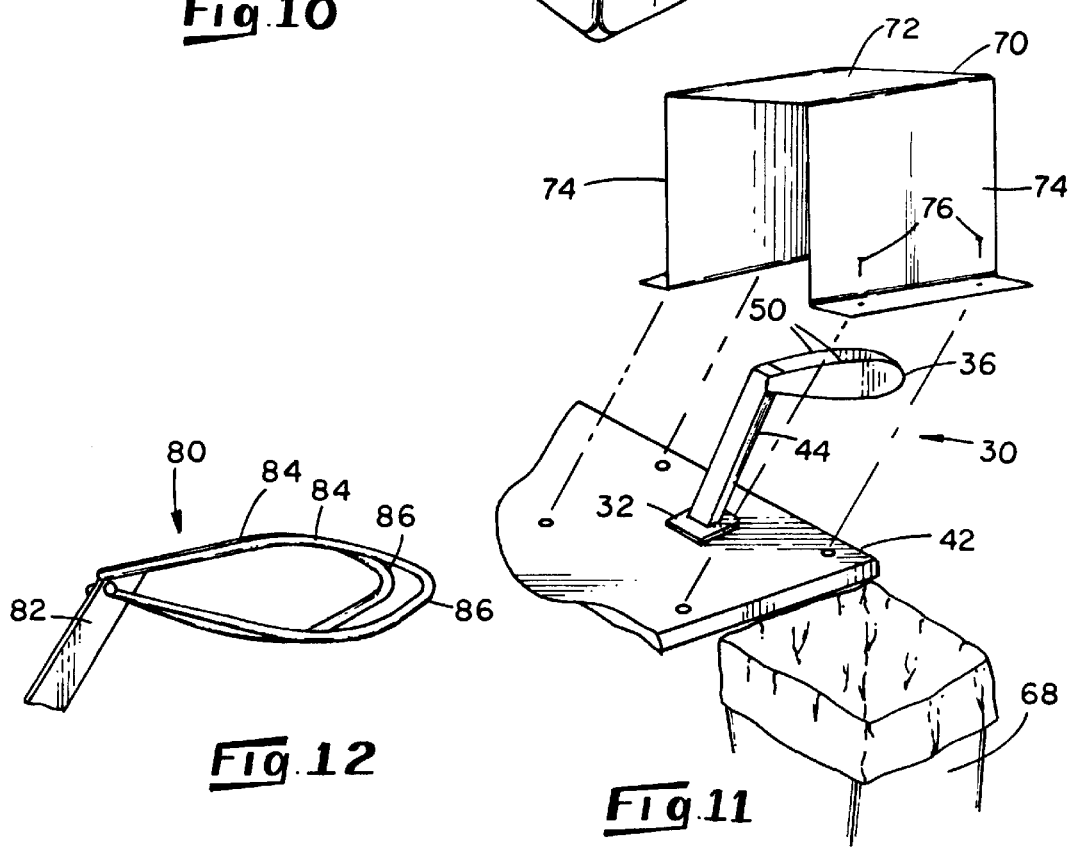
_Fig.12_                    _Fig.11_

APPARATUS FACILITATING THE REMOVAL OF A LATEX GLOVE FROM THE HAND OF A WEARER

BACKGROUND OF THE INVENTION

This invention relates generally to accessories for the medical field and relates, more particularly, to the means and methods by which a latex glove is removed from the hand of medical personnel, such as a surgeon, following use of the glove.

Small, tight-fitting latex gloves (also known as latex surgical gloves) are commonly worn by medical personnel to provide a barrier between the skin of the hands wearing the gloves and contaminated fluids and/or contaminated contact surfaces. Heretofore, however, the removal of the used gloves from the hands of the medical personnel has been difficult in that the gloves were hard to remove without contacting the exterior (and possibly contaminated) surface of the gloves. Some medical personnel, notably a surgeon, enlists the aid of another individual, such as surgery room assistant, who, while wearing his own latex gloves, pulls the used gloves from the hands of the personnel wearing the gloves. Of course, such a removal technique is likely to expose the skin of the other individual to contact with the exterior surfaces of the used gloves.

It is an object of the present invention to provide an apparatus which facilitates the removal of a latex glove from the hand of a wearer which reduces any risk of exposure to an exterior surface of the glove and which does not require the assistance of another individual to remove the glove.

Another object of the present invention is to provide such an apparatus which facilitates the simultaneous removal of a pair of latex gloves worn upon both hands of a wearer.

Yet another object of the present invention is to provide such an apparatus which is uncomplicated in construction yet effective in operation.

SUMMARY OF THE INVENTION

This invention resides in an apparatus facilitating the removal of a latex glove from the hand of a wearer wherein the glove includes a finger-providing portion and a cuff portion joined to the finger-providing portion.

The apparatus includes a support base and means attached to the support base providing an arcuate edge having a bend therealong which is projected in a first direction. The bend is sized to be accepted by the cuff portion of the glove so that by sliding the inside of the forearm of the glove-wearing hand relative to and along the arcuate edge-providing means in a direction opposite the first direction, the cuff portion of the glove accepts and becomes hooked upon the arcuate edge and so that continued movement of the forearm in the direction opposite the first direction backs the hand out of the glove.

BRIEF DESCRIPTION OF THE DRAWINGS

FIG. 1 is a perspective view of a pair of latex gloves worn upon by the hands of a wearer.

FIG. 2 is a perspective view of an embodiment of an apparatus within which features of the present invention are embodied and a fragment of a table to which the apparatus is secured.

FIG. 10 is a perspective view of the FIG. 2 apparatus shown being used to simultaneously remove gloves worn by both hands of a wearer.

FIG. 11 is a perspective view of the FIG. 2 apparatus accompanied by a protective hood.

FIG. 12 is a perspective view of a fragment of an alternative embodiment of an apparatus within which features of the present invention are embodied.

DETAILED DESCRIPTION OF THE ILLUSTRATED EMBODIMENT

Figure 3:
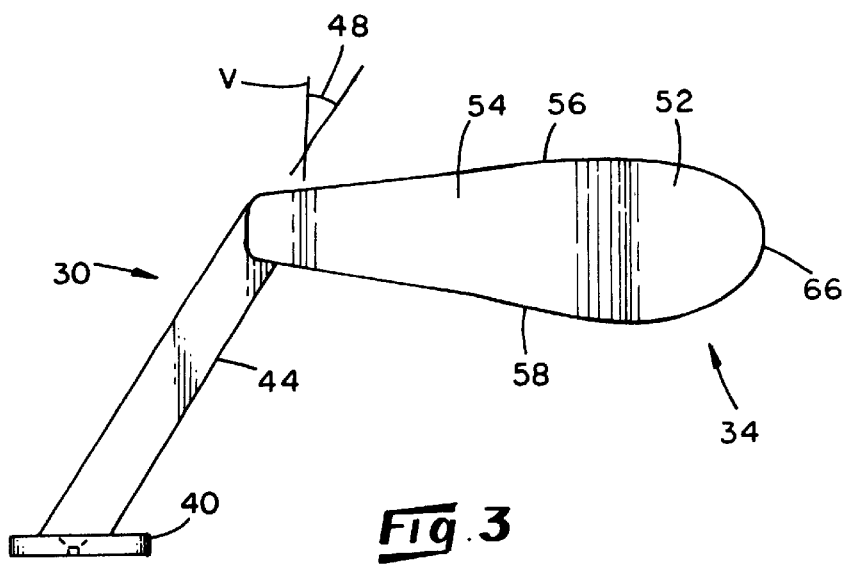
FIG. 3 is a side elevational view of the FIG. 2 apparatus as seen generally from the right in FIG. 2.
Figure 4:
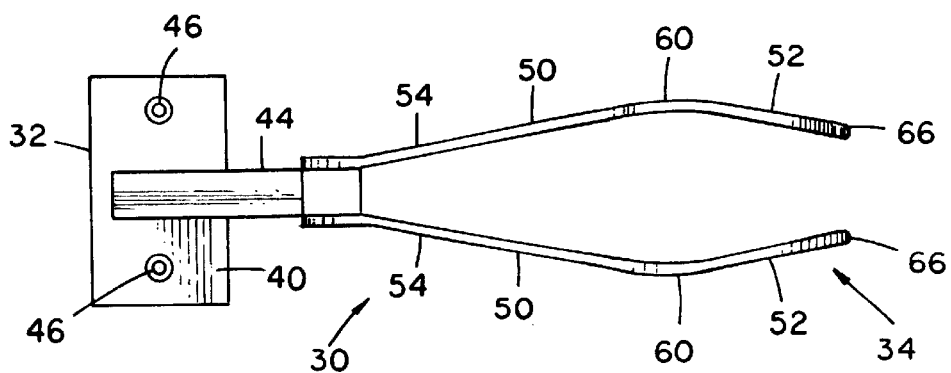
FIG. 4 is a plan view of the FIG. 2 apparatus as seen from above in FIG. 3.
Figure 5:
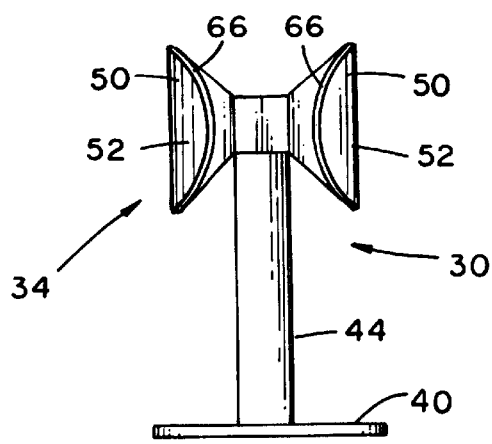
FIG. 5 is a front elevational view of the FIG. 2 apparatus as seen from the right in FIG. 3.

Turning now to the drawings in greater detail, there is illustrated in FIG. 1 an example of a pair of latex gloves (also known as latex surgical gloves), each indicated 20, of a class capable of being removed with the aid of an apparatus of the present invention. More specifically, each glove 20 includes an elongated fingered hand portion 24 and a cuff portion 26 which is integrally joined to the hand portion 24. As used herein, the term "cuff portion" is intended to mean that part of the glove 20 intended to cover or encircle the wrist, indicated 27, of a wearer 29. In addition, the glove 20 is formed of a latex material and is thin-walled so that the glove 20 possesses a large degree of flexibility. As used, herein, the term "latex" is intended to include any of a number of elastomeric materials, such as rubber or synthetic rubber, which is capable of being used to construct flexible, thin-walled gloves.

An example of a glove which can be used as the glove 20 is available from Mabco Products Inc. of Bound Brook, N.J. under the trade designation Yes.

With reference to FIGS. 2–5, there is illustrated an embodiment of an apparatus, generally indicated 30, which can be used to readily and quickly remove a glove 20 (FIG. 1), as well as a pair of gloves 20, from the hand, or hands, of the wearer 29 without requiring contact between the wearer's hands or, more specifically, the skin of the wearer's hands and an exterior surface of the glove 20. Thus, the apparatus 30 is well-suited for use in an environment, such as that of a surgery room, in which removal of a glove 20 following use thereof is desired to be as hands-free as possible to avoid contact with contaminated fluids or other substances which may be present on the exterior surface of the glove 20 to the skin of the wearer or the wearer's assistant.

The apparatus 30 includes a support base 32 and means, generally indicated 34, joined to the support base 32 for providing at least one arcuate edge 36 having a bend 38 capable of acceptance by the cuff portion 26 of a glove 20 when worn upon a hand. The support base 32 of the depicted apparatus 34 includes a base portion 40 adapted to rest upon a table 42 or similar support surface and a pedestal portion 44 which is joined to so as to extend upwardly from the base portion 40.

The base portion 40 is plate-like in form and has a rectangular shape which is arranged so that the plane of its rectangular shape is oriented generally horizontal. In addition, the base portion 40 has a plurality (i.e. two) of openings 46 adjacent two of its side edges to accept the shanks of bolts 48 used to rigidly secure the base portion 40 to the table 42. In this connection, the shanks of the bolts 48 are directed downwardly through pre-formed openings provided in the table 42, and nuts 49 (only one shown in FIG. 2) are tightly threaded upon the ends of the bolt shanks so that the apparatus 30 is firmly secured to the table 42 between the nuts 49 and the heads of the bolts 48. As will be apparent herein, the apparatus 30 is exposed to forces as a glove 20 is pulled from the wearer's hand with the apparatus 30. Consequently, the securement between the base portion 40 and the table 42 must render the apparatus 30 stable enough to resist such pulling-induced forces.

The pedestal portion 44 is elongated in shape with a substantially square cross section. In addition, the lower end, as viewed in FIG. 3, of the pedestal portion 44 is shaped so that when positioned against and joined to the base portion 40, the upper end of the pedestal portion 44 extends upwardly, yet is slightly canted with respect to the vertical so that the upper end of the pedestal portion 44 leans forwardly of the base portion 40. For present purposes, the forward edge of the base portion 40 is that edge which corresponds with the direction that the upper end of the pedestal portion 44 leans with respect to the vertical. In the depicted embodiment 30, the pedestal portion 44 forms an angle 48 of about thirty degrees with the vertical, indicated V in FIG. 3.

With reference still to FIGS. 2–5, the arcuate edge-providing means 34 of the depicted embodiment 30 includes a pair of elongated blade-like members 50 each having a planar forward end, or tip, portion 52 and a rearward end portion 54 and smooth upper and lower edges 56 and 58 which extend between the forward and rearward end portions 52 and 54. In addition, each blade-like member 50 is formed from a single flat piece of metal having two flat sides which is bent between its end portions 52 and 54 so as to form a shallow V having an apex 60, and the rearward end portions 54 of the blade-like members 50 are arranged on opposite sides of the pedestal portion 44 at the upper end thereof and are joined to the pedestal portion 44, as with welds, to secure the blade-like members 50 to the pedestal portion 44. Further still, the blade-like members 50 are arranged on the opposite sides of the pedestal portion 44 so that the apexes 60 of the members 50 are directed away from one another and the forward end portions 52 are spaced from one another by a short distance, such as about 1.0 inches. Yet further still, the blade-like members 50 are arranged in somewhat of a parallel relationship in that the general platen-like shape of each member 50 is arranged in a vertical plane which is somewhat parallel to the vertical plane in which the platen-like shape of the other member 50 is arranged.

To facilitate the removal of gloves 20 from the hands of a wearer and as will be apparent herein, the forward end portion 52 of each blade-like member 50 includes the earlier-mentioned arcuate edge 36 which is directed forwardly of the base 32 and which is sized to be accepted by a glove 20 as the hand which is wearing the glove 20 is directed wrist-end-first over the edge 36. Accordingly, the forwardly-directed edge 36, while arcuate in shape, is pointed enough to facilitate the entry of the edge 36 between the wrist of the wearer's hand and the cuff portion 26 of the glove 20. As will be apparent herein, this entry of the edge 36 into the cuff portion 26 hooks the glove 20 upon the edge 36 so that continued (sliding) movement of the hand, or more specifically the wearer's forearm, in a rearward direction along a side surface of the blade-like member 30 backs the hand out of the glove 20.

The material out of which the apparatus 30 is constructed, including the base 32 and the arcuate edge-providing means 34, is steel, but other materials can be used. To enable the apparatus 30 to be readily sterilized, it is preferable that the apparatus 30 be constructed of stainless steel.

Figure 6:
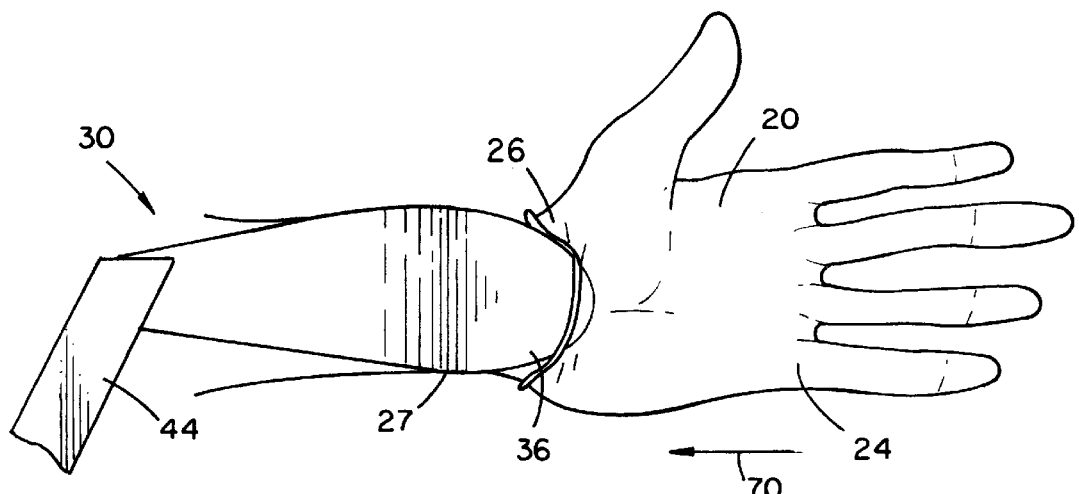
FIGS. 6–9 are fragmentary views of the FIG. 2 apparatus shown with one of its blades removed and being used to remove a glove from the left hand of a wearer.

To use the apparatus 30 to remove a glove 20, the wearer positions the inside surface of the forearm of the glove-wearing hand against one of the side surfaces (i.e. the outwardly-directed side surface) of one of the blade-like members 50 so that the glove-wearing hand is disposed forwardly of the arcuate edge 36. The forearm is then slid rearwardly along the outer surface of the blade-like member 50 from the arcuate edge 36 thereof (i.e. in the direction of the arrow 70) so that the cuff portion 26 of the glove 20 becomes hooked upon the arcuate edge 36 of the member 30 at the wrist of the hand, as shown in FIG. 6. Because the outer surface of the member 30 is relatively smooth, the skin of the forearm and wrist of the glove-wearing hand slides unobstructed along the member 30 so that the entry of the cuff portion 27 into the glove 20 requires very little manipulation of the hand to direct the arcuate edge 36 of the member 50 into the glove 20. Thus, little time is necessary to hook the cuff portion 26 of the glove 20 upon the arcuate edge 36.

As the cuff portion 26 becomes hooked upon the arcuate edge 36, the arcuate edge effectively grabs the inside surface of the glove 20 at about the palm region thereof due, at least in part, to the frictional-gripping engagement between the glove 20 and the member 50 and the proximity of the arcuate edge 36 to the fingers of the glove 30—into which the arcuate edge 36, because of its size, cannot extend. Moreover, the latex material of the glove 20, as is the case with most gloves of this class, resists tearing as it is pulled against the arcuate edge 36.

Figure 7:
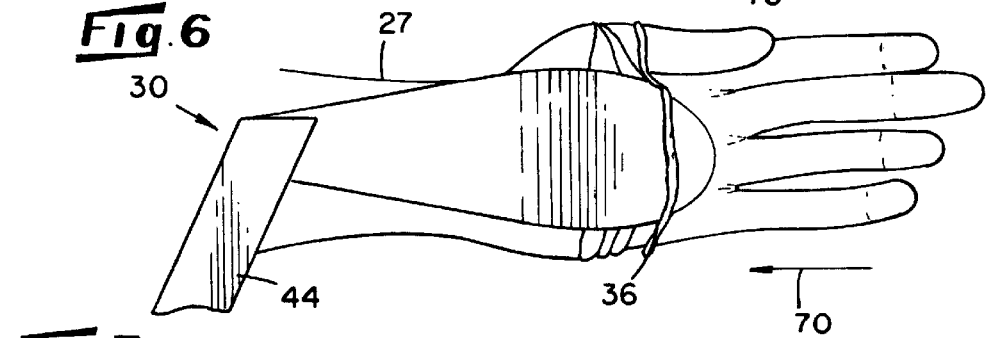
Figure 8:
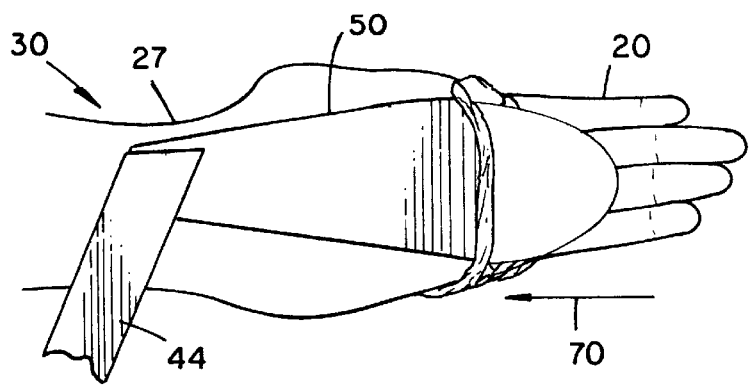
Figure 9:
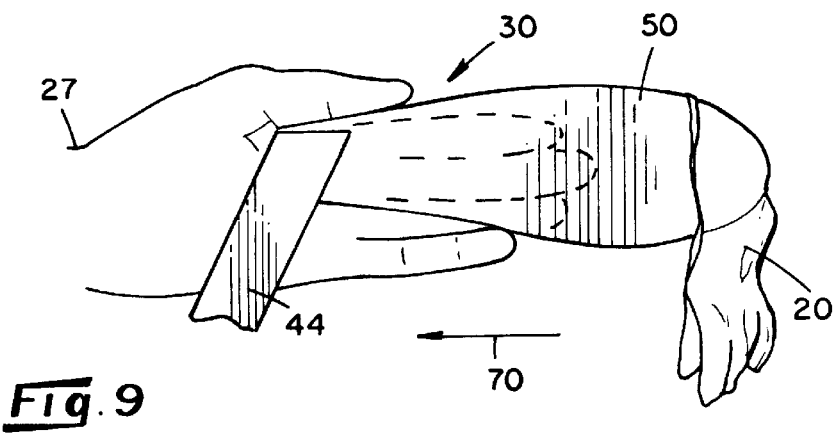

With the cuff portion 26 hooked upon the arcuate edge 36, the continued rearwardly-directed motion of the forearm of the glove-wearing hand along the member 50 backs the hand out of the glove 20 as illustrated in the sequential views of FIGS. 7–9. In this connection and as the forearm continues to be slid rearwardly along the outer surface of the member 50 and as illustrated in FIG. 8, the hand continues to back out of the glove 20 as the glove 20 remains hooked upon the arcuate edge 36 of the member 50. Complete withdrawal of the hand from the glove 20 is effected when the fingers of the hand are backed out of the fingers of the glove 20 as illustrated in FIG. 9. It will be understood that as the hand is backed out of the glove 20, the glove 20 usually turns inside out. Such a consequence, however, is normally of little concern since in most medically-related uses, latex gloves are used only once before being discarded. On occasion, the glove 20 remains hooked to the arcuate edge 36 of the member 50 upon complete removal of the hand from the glove 20, but more likely than not, when the glove 20 is removed from the hand in a relatively rapid motion so that the material of the glove 20 stretches slightly during the glove-removal process, the resiliency of the glove 20 throws the glove 20 from the arcuate edge 36.

The apparatus 30 is particularly well-suited for removing the gloves 20 simultaneously from both hands of the wearer. In this connection and with reference to FIG. 10, the wearer 29 stands rearwardly of the apparatus 30 and positions the inside surfaces of his forearms against the outer side surfaces of the blade-like members 50. In other words, the inside surface of each forearm is positioned against the outside surface of a corresponding blade-like member 50 so that his hands are positioned forwardly of the arcuate edges 36. With his hands and forearms positioned in such manner, the wearer slides his forearms rearwardly along the outer surfaces of the members 50 so that the cuff portions 26 of the gloves 20 become hooked upon the arcuate edges 36 of the members 50 as illustrated in FIG. 10. As the wearer continues to slide his forearms rearwardly along the outer surfaces of the members 50, the hands back completely out of the gloves 20. Upon removal of the wearer's hands from the gloves 20, the gloves 20 are free to fall into a trash receptacle 68 situated beneath the arcuate edge 36 of the apparatus 30 for disposal. Accordingly, it is preferred that the apparatus 30 be mounted upon a table 42 so that the arcuate edge 36 of the apparatus 30 overhangs an edge of the table 42, and a trash receptacle 68 is positioned directly beneath the receptacle 68. Thus, the apparatus 30 facilitates the simultaneous and relatively rapid removal of the gloves 20 from both hands of the wearer and is advantageous in this respect.

If desired and as depicted in FIG. 11, the apparatus 30 can be used with a protective hood 70 to further prevent the exposure of a wearer, or his surroundings, to the exterior surfaces of the gloves 20 upon removal of the gloves 20 from the wearer's hands. In the depicted FIG. 11 environment, the hood 70 has been formed to include a top 72 and two sides 74 which can be secured to the top of the table 42 with screws 76. The hood 70 is positionable over the apparatus 30 so that hands of a wearer can be inserted through the opening (provided between the sides 74) at the rear of the hood 70 and manipulated against the blade-like members 50 in the aforedescribed manner for removal of the gloves from the wearer's hands. During a glove-removal operation, the protective hood 70 serves as a barrier between the face of the wearer and the gloves being removed and prevents any substance from being inadvertently thrown or splashed from the exterior surface of the gloves toward the wearer's face. Again and as is the case with the environment depicted in FIG. 10, upon removal of the gloves from the wearer's hands with the apparatus 30 in the FIG. 11 environment, the removed gloves are free to fall into the trash receptacle 68 for disposal.

It will be understood that numerous modifications and substitutions can be had to the aforedescribed embodiment without departing from the spirit of the invention. For example, although the arcuate edge-providing means 34 of the embodiment 30 has been shown and described as including a pair of blade-like members 50, such edge-providing means 34 can take alternative forms. For example, there is illustrated in FIG. 12 an embodiment of a glove-removing apparatus 80 having a base support 82 and edge-providing means in the form of a pair of wire loops 84 which have each been rigidly attached to the support 82 and are formed so as to provide a forwardly-directed arcuate edge 86. Like the arcuate edge 36 of each blade-like member 50, the wire-defining arcuate edge 86 of the embodiment 80 is sized to be accepted by the cuff portion of a glove so that by sliding the inside of the forearm of the glove-wearing hand relative to and along the arcuate edge 86 in a rearwardly direction, the cuff portion of the glove accepts and becomes hooked upon the arcuate edge 86 and so that continued movement of the forearm in the rearward direction backs the hand out of the glove. Accordingly, the aforedescribed embodiment is intended for the purpose of illustration and not as limitation.

What is claimed is:

1. In combination, an apparatus facilitating the removal of a latex glove from the hand of a wearer who is wearing the glove and a protective hood which is positionable about the apparatus so as to provide a barrier between the face of the wearer and the wearer's hand during a glove-removal operation wherein the glove includes a finger portion disposed about the fingers of the wearer's hand and a cuff portion attached to the finger portion so as to encircle the wrist of the wearer's hand, the apparatus comprising:

a support base which is securable in a stationary condition relative to a tabletop or other stationary support surface; and a pair of blade-like members which are rigidly attached to the support base and wherein each blade-like member includes a tip portion having an arcuate edge which is projected in a first direction, and the arcuate edge is sized to be accepted by the cuff portion of the glove while the glove is being worn upon the hand of the wearer so that the cuff portion of the glove encircles the wrist of the wearer's hand so that by sliding the inside of the forearm of the glove-wearing hand relative to and along one side of the blade-like member in a direction opposite the first direction, the cuff portion of the glove which encircles the wrist of the wearer's hand accepts and becomes hooked upon the arcuate edge at the wearer's wrist and so that continued movement of the forearm in the direction opposite the first direction backs the hand out of the glove while the cuff portion of the glove remains hooked upon the arcuate edge; and wherein the pair of blade-like members are supported by the support base in a substantially parallel relationship and so that the tip portions thereof are both directed generally in the first direction so that a pair of gloves can be simultaneously removed from the hands of the wearer as the wearer slides the inside surfaces of the forearms of his glove-wearing hands relative to and along the sides of the blade-like members in a direction opposite the first direction so that the cuff portions of the gloves are accepted and become hooked upon the arcuate edges and so that continued movement of the forearms in the direction opposite the first direction backs the hands out of the gloves.

2. The combination as defined in claim 1 wherein the tip portion of each blade-like member is contained substantially within a plane.

3. The combination as defined in claim 1 wherein each blade-like member is smooth-surfaced.

4. The combination as defined in claim 1 wherein the base of the apparatus includes an attachment portion and a pedestal portion attached to the attachment portion and having an upper end which extends generally upwardly from the attachment portion, and the pair of blade-like members are attached to the upper end of the pedestal portion.

5. The combination as defined in claim 1 wherein tip portion of each blade-like member is substantially planar in form, and the plane of each blade-like member is oriented substantially vertically when the support base is secured in a stationary condition relative to a tabletop or other stationary support surface and each blade-like member includes an outwardly-directed surface which is directed away from the other blade-like member and along which the inside of the user's forearms can be slid in a glove-removing operation.

6. An apparatus facilitating the removal of a pair of latex gloves from the hands of a wearer who is wearing the gloves and wherein each glove includes a finger-providing portion disposed about the fingers of the wearer's hand and a cuff portion attached to the finger portion so as to encircle the wrist of the wearer's hand, the apparatus comprising:

a support base including an attachment portion which is securable in a stationary condition relative to a tabletop or other stationary support surface and a pedestal portion attached to the attachment portion, the pedestal portion having an end which extends generally away from the attachment portion;

a pair of blade-like members which are joined to said end of the pedestal portion and wherein each blade-like member has two opposite end portions and is bent between its end portions so as to form a shallow V therebetween, and the blade-like members are supported by the pedestal in spaced relationship with one another and so that the shallow V of blade-like members oppose one another and so that one end portion of each blade-like member projects in a first direction and is in a side-by-side relationship with the one end portion of the other blade-like member; and each of said one end portion of the blade-like member terminates in a tip having a bend which is sized to be accepted by the cuff portion of a glove while the glove is being worn upon the hand of the wearer so that the cuff portion of the glove encircles the wrist of the wearer's hand so that by sliding the inside of the forearm of a glove-wearing hand relative to and along one of the blade-like members in a direction opposite the first direction, the cuff portion of the glove which encircles the wrist of the wearer's hand accepts and becomes hooked upon the bend of the one end portion of the corresponding blade-like member and so that continued movement of the forearm in the direction opposite the first direction backs the hand out of the glove while the cuff portion of the glove remains hooked upon the bend of the one end portion.

7. A method of removing a latex glove from the hand of a wearer wherein the glove includes a finger-providing portion and a cuff portion joined to the finger-providing portion, the method comprising the steps of:

providing an apparatus including a support base and means attached to the support base providing an arcuate edge having a bend therealong which is projected in a first direction, and the bend is sized to be accepted by the cuff portion of the glove so that by sliding the inside of the forearm of the glove-wearing hand relative to and along the arcuate edge-providing means in a direction opposite the first direction, the cuff portion of the glove accepts and becomes hooked upon the arcuate edge and so that continued movement of the forearm in the direction opposite the first direction backs the hand out of the glove;

sliding the inside of the forearm of the glove-wearing hand relative to and along the arcuate edge-providing means in a direction opposite the first direction so that the cuff portion becomes hooked upon the arcuate edge without the aid of another hand; and continuing the movement of the forearm in the direction opposite the first direction so that the hand backs out of the glove.

* * * * *